Figure 1:
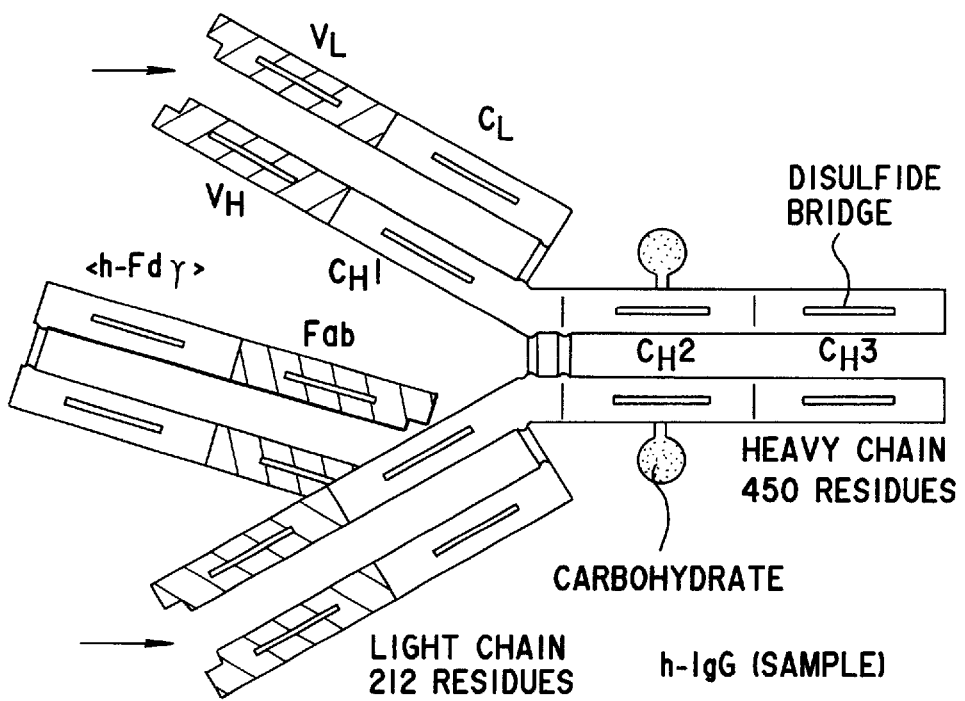

United States Patent [19]
Klemt et al.

[11] Patent Number: 5,804,391
[45] Date of Patent: Sep. 8, 1998

[54] ELIMINATION OF RHEUMATOID FACTOR INTERFERENCE USING ANTI-FD ANTIBODIES

[75] Inventors: Volker Klemt, Weilheim; Dittmar Schlieper, Iffeldorf; Urban Schmitt, Oberhausen; Michael Wiedmann, Penzberg, all of Germany

[73] Assignee: Boehringer Mannheim GmbH, Mannheim, Germany

[21] Appl. No.: 817,089

[22] PCT Filed: Nov. 2, 1995

[86] PCT No.: PCT/EP95/04308

§ 371 Date: Apr. 11, 1997

§ 102(e) Date: Apr. 11, 1997

[87] PCT Pub. No.: WO96/14338

PCT Pub. Date: May 17, 1996

[30] Foreign Application Priority Data

Nov. 4, 1994 [DE] Germany .......................... 44 39 452.7

[51] Int. Cl.$^6$ ........................ G01N 33/536; G01N 33/543
[52] U.S. Cl. ......................... 435/7.1; 435/7.5; 435/7.94; 435/7.95; 435/962; 436/509; 436/512; 436/513; 436/518; 436/536; 436/825

[58] Field of Search ............................ 435/7.1, 7.5, 7.94, 435/7.95, 962; 436/509, 512, 513, 518, 825, 536

[56] References Cited

U.S. PATENT DOCUMENTS 5,466,611  11/1995  Toth ........................................ 436/534

FOREIGN PATENT DOCUMENTS 0 292 810     5/1988   European Pat. Off. .
42 02 923 A1  8/1993   Germany .

OTHER PUBLICATIONS

Patent Abstracts of Japan, vol. 006 No. 073, Aug. 5, 1982, JP,A,57 009723.

The Journal of Rhuematology, vol. 12, No. 3, Jun. 1985, pp. 427–431, Powell et al., An Improved assay for IGG Rhematoid Factor . . . .

*Primary Examiner*—David Saunders
*Attorney, Agent, or Firm*—Nikaido Marmelstein Murray & Oram, LLP

[57] ABSTRACT

The invention concerns the use of a composition which is composed of several different antibodies or/and antibody fragments which serves as a reagent to eliminate rheumatoid factor interference in an immunochemical method.

15 Claims, 2 Drawing Sheets

ELIMINATION OF RHEUMATOID FACTOR INTERFERENCE USING ANTI-FD ANTIBODIES

DESCRIPTION

The invention concerns the use of a composition composed of several different antibodies or/and antibody fragments as a reagent to reduce interferences caused by rheumatoid factors in an immunochemical method.

The mammalian organism contains various classes of antibodies which are formed by the B cells of the immune system to defend against antigens. The antibody molecules are composed of one or several sets of four polypeptide chains, two heavy chains and two light chains which are linked together via disulfide bridges.

Antibodies are generally divided into the classes G, M, A, D and E. These five immunoglobulin classes differ in their heavy chain which is denoted γ, μ, α, δ and ε chain. In addition there are also immunoglobulin subclasses in the case of IgG, IgA and IgM.

Antibodies of the IgG class constitute 70 to 75% of the total immunoglobulin in normal human serum (corresponding to 8 to 16 mg/ml). They are mainly formed as the secondary immune response of the organism to an infection.

Antibodies of the IgM class make up ca. 10% of the immunoglobulin present in human serum and have a pentameric structure. These antibodies appear very early after an infection so that their determination is important for the early detection of diseases.

The immunoglobulins of the IgA class form about 15 to 20% of the immunoglobulin present in human serum and are the most important secretory immunoglobulin in saliva, milk and secretions of the urogenital region.

Antibodies of the IgD class are located on the membrane of circulating B cells and it is assumed that they play a role in autoimmune diseases.

Antibodies of the IgE class only occur in a very small amount in serum, but they play an important role in a number of allergic reactions such as asthma and hayfever.

The class-specific determination of immunoglobulins i.e. the selective determination of antibodies of one or several selected immunoglobulin classes or subclasses which are directed against a particular antigen in the presence of antibodies of other immunoglobulin classes or subclasses which are directed against the same antigen is of particular importance for the detection of particular diseases e.g. for the early diagnosis of infections, to differentiate between acute and healed infections and to make precise prognoses.

Methods for the class-specific determination of immunoglobulins are known. For this an immune component that is specific for a selected antibody class e.g. an antibody against the μ chain of human IgM can be coupled to a solid carrier and the antigen-specific immunoglobulin component can be detected by reaction with a directly or indirectly labelled antigen. In this type of method and also in other immunological test systems rheumatoid factors i.e. anti-IgG autoantibodies can interfere with the determination of the analyte. This can result in a falsification of the results and in particular false-positive reactions may occur.

EP-A-0 163 312 discloses an immunological test procedure in which particles which have an average size of ≦0.2 μm and are coated with an interference-eliminating substance are used to inhibit an unspecific immune reaction. Immunoglobulins of human or animal origin are cited as interference-eliminating substances.

Henle et al. (Clin. Exp. Immunol. 36 (1979), 415–422) describe rheumatoid factors as the cause of false-positive reactions in tests for immunoglobulins that are specific for Epstein-Barr-Virus. It was possible to eliminate the interferences in some cases by using IgG-coated latex particles. Ho et al. (J. Clin. Microbiol. 27 (1989), 952–958) also describe the elimination of interference in an indirect ELISA for specific anti-Epstein-Barr-Virus antibodies by adding latex particles coated with human IgG.

Torfason and Diderholm (J. Med. Virol. 10 (1982), 157–170) disclose the fact that rheumatoid factors can lead to false results in the determination of IgM immunoglobulins against herpes simplex virus and cytomegalovirus. A mixture of protein A-Sepharose and protein A-Sepharose saturated with human IgG is cited as an interference-eliminating reagent.

The elimination of interference by rheumatoid factors of the classes IgM, IgA and IgG by the addition of dithiothreitol (DTT) is described by Espersen et al. (Scand J. Rheumatology 75 (1988), 40–45).

EP-B-0 292 810 discloses a method for the determination of antigen-specific antibodies from one of the immunoglobulin classes M, A, D and E in a sample liquid wherein an interference-eliminating reagent is added to avoid interferences by antibodies of the IgG class which is selected from anti-human IgG, aggregated human or animal IgG or a γ-Fc fragment. The interference-eliminating reagent is intended to eliminate the antigen binding of the specific IgG antibodies present in the sample and to suppress the activity of rheumatoid factors.

DE-OS 42 02 923 describes the elimination of interference by rheumatoid factors by adding non-specific immune complexes. These immune complexes contain antibodies from immunized animals which are directed against an antigen which is not the analyte.

A method for diagnosing acute infections by an IgM antibody determination without interference by rheumatoid factor is described by R. Ziegelmaier et al. ("Larboratoriumsblätter" 33 (1983), 19–25). Aggregated γ globulin, IgG-coated polystyrene particles, staphylococcal A-protein and anti-human IgG γ chain are cited as interference-eliminating reagents.

Martins et al. (Clin. Diagnost. Laboratory Immunol. 2 (1995), 98–103) describe an assessment of the effectiveness of three procedures for removing immunoglobulin G for the class-specific detection of IgM immunoglobulins. It was found that anti-human IgG antibodies are more effective than recombinant protein G.

However, the reagents of the state of the art for eliminating interference have some disadvantages. Thus insoluble immune complexes are produced which can lead to a turbidity in the sample and may interfere with the measurement. More importantly the disclosed reagents are not able to completely eliminate the interferences by rheumatoid factors so that even when sedimentation occurs the test may still be falsified. Moreover when anti-human IgG antibodies are used the concentration of the reagent has to be adjusted exactly since an excess can lead to a dissolution of the precipitate.

The German Patent Application P 44 39 452.7 describes a composition composed of several different antibodies or/and antibody fragments which is suitable as a reagent for eliminating interference in an immunochemical method for the class-specific detection of antibodies from one or several of the immunoglobulin classes G, M, A, D and E. These antibodies or/and antibody fragments are specific for the Fd section of the heavy chain of immunoglobulins. Furthermore the use of the composition is proposed in an immunoassay for the selective class-specific determination of antibodies of the classes IgG, IgM, IgA, IgD or/and IgE in order to suppress interferences caused by antibodies of other classes. Examples are not described in which an elimination of interference by rheumatoid factors is shown.

The object of the present invention was to provide a method for the elimination of interference by rheumatoid factors which enables the disadvantages of the state of the art to at least be substantially avoided.

This object is achieved by the use of a composition composed essentially of several different antibodies or/and antibody fragments which is specific for the Fd section of the heavy chain of immunoglobulins of one or several of the classes IgG, IgM, IgA, IgD and IgE and at least substantially masks the ability of these immunoglobulins to bind antigens, as a reagent for reducing interferences caused by rheumatoid factors in an immunochemical method for the determination of an analyte.

The use according to the invention of an anti-Fd antibody or/and antibody fragment composition in an immunochemical method surprisingly results in a substantial or complete elimination of interference by rheumatoid factors. The use is particularly preferred in the case of test procedures for the determination of IgM antibodies in which rheumatoid factors, usually rheumatoid factors of the IgM class, which are directed unspecifically towards IgG antibodies and in particular towards human IgG antibodies have caused considerable problems in the methods of the state of the art.

A number of advantages are achieved compared to the known methods of interference elimination from the state of the art. Thus in the method according to the invention a sample pre-treatment is not required i.e. the anti-Fd composition can be added at the same time as other test components. Furthermore the addition of the anti-Fd composition does not cause formation of precipitates or a concomitant interference of the test. This enables a more simple and thus more reliable control of the reagents and a better lot to lot constancy. In addition a considerable reduction of the risk of carry-over is found in measurements on automated analyzers.

The anti-Fd reagent binds to that region of the heavy chain of immunoglobulins which lies between the antigen binding site and the hinge region (in the region of the $V_H$ and the $C_H^1$ domain; cf. FIG. 1). The binding sites are preferably in the constant region of the $C_H^1$ domain of the immunoglobulins i.e. in the $C_{\alpha H}^1, C_{\delta H}^1, C_{\epsilon H}^1, C_{\gamma H}^1, C_{\mu H}^1$ region (cf. "Kurzes Lehrbuch der Immunologie", I. M. Roitt; Thieme Verlag, Stuttgart, New York (1987), chapter 5: "Antikörper: Struktur und Funktion", p. 49 ff). Amino acid sequences of these domains are described for example in Kabat et al., Sequences of Proteins of Immunological Interest, 5th ed. (1992), U.S. Department of Health and Human Services, USA.

The elimination of interference by rheumatoid factors by using the anti-Fd reagent can be utilized for the immunochemical determination of any desired analytes e.g. antigens such as peptides, polypeptides, glycoproteins, hormones, mediators, neurotransmitters, metabolites, surface structures of cells or viruses etc. and also for the specific determination of antibodies. The determination of antibodies against pathogens such as viruses, bacteria or other microorganisms or of autoimmune antibodies is preferred. The determination is preferably carried out in body fluids especially in human body fluids such as serum, blood, plasma, saliva and urine in which rheumatoid factors may be present.

The composition is specific for the Fd section of the heavy chain i.e. it is essentially free of components which could react with the Fd section of a light chain i.e. a κ or λ chain. The maximum cross-reactivity with a light immunoglobulin chain is preferably $10^{-1}$ and particularly preferably $10^{-2}$ relative to the reactivity with the heavy chain.

The antibody or/and antibody fragment composition can be added in a 5-fold molar excess relative to the rheumatoid factors that are to be masked whose interfering effect is preferably inhibited by at least 50%, particularly preferably by at least 90% and most preferably by at least 99%.

The composition used according to the invention is preferably specific for a first immunoglobulin class selected from the classes IgG, IgM, IgA, IgD and IgE and has a maximum cross-reactivity with another immunoglobulin class of $10^{-2}$, particularly preferably $10^{-3}$ relative to the reactivity towards the first immunoglobulin class.

In a preferred embodiment of the invention the antibody or/and antibody fragment composition is specific for the Fd section of the heavy chain of immunoglobulin G in particular of human immunoglobulin G. This composition is especially suitable for the class-specific determination of antibodies from one or several of the classes IgM, IgA, IgD and IgE in the presence of rheumatoid factors i.e. anti-IgG antibodies and optionally competing antibodies of the IgG class. Such a composition preferably has a maximum cross-reactivity with another immunoglobulin class such as IgM of $10^{-2}$, particularly preferably $10^{-3}$ relative to the reactivity towards IgG.

For some applications it may be preferable for the composition to be species-specific for human immunoglobulin and have a maximum cross-reactivity with non-human immunoglobulin of $10^{-2}$, particularly preferably of $10^{-3}$ relative to the reactivity towards human immunoglobulin.

The composition used according to the invention is composed of antibodies or/and antibody fragments. The composition is preferably composed of monovalent antibody fragments e.g. Fab fragments which are obtainable by enzymatic cleavage of antibodies with papain and subsequent fractionation of the cleavage products. If a composition is used composed of monovalent antibody fragments this avoids sedimentation of the masked antibodies.

The composition according to the invention is composed of several different antibodies or/and antibody fragments which are each specific for different regions of the Fd section of the heavy immunoglobulin chain. The composition is preferably composed of polyclonal antibodies or/and antibody fragments, it can, however, also be composed of a mixture of at least two and preferably of at least three and particularly preferably of at least four different monoclonal antibodies or/and antibody fragments.

A polyclonal antibody or/and antibody fragment composition used according to the invention is obtainable by a process in which (a) an experimental animal is immunized with an immunogen which contains the Fd section of the heavy chain of immunoglobulins from a first immunoglobulin class, (b) a polyclonal antiserum is obtained from the experimental animal, (c) the polyclonal antiserum is optionally converted by cleavage into monovalent antibody fragments, (d) the antiserum or the monovalent antibody fragments are subjected to one or several immunosorption steps which allow a selection for antibodies or/and antibody fragments which are specific for the Fd section of the heavy chain of the first immunoglobulin class and (e) an antibody or antibody fragment composition with a specificity for the Fd section of the first immunoglobulin class is isolated.

The use of a suitable immunogen in combination with carrying out suitable immunosorption steps enables an antibody or antibody fragment composition to be isolated which is specific for the Fd section of the heavy chain of one or several selected immunoglobulin classes and preferably has essentially no cross-reactivity with other immunoglobulin classes or immunoglobulins from a species that is foreign to that of the selected classes. Whole antibodies, antibody fragments such as antibody fragments produced by enzymatic cleavage such as Fab, Fab' or F(ab)'$_2$ or recombinant antibody fragments, peptide epitopes or mixtures thereof can for example be used as immunogens. The use of immunogens which are free of antibody Fc components is preferred. In this manner it is possible to substantially avoid the formation of anti-Fc antibodies in the experimental animal e.g. a sheep, a rabbit or a mouse.

The immunosorption steps of the process according to the invention preferably comprise (i) at least one positive immunosorption against an antigen which contains the Fd section of the heavy chain of the first immunoglobulin class and the isolation of binding components of the composition which specifically recognize the Fd section of the heavy chain of the first immunoglobulin class. If an immunogen is used which contains the Fd section of the heavy chain of immunoglobulin G e.g. an Fab fragment, the antiserum or the antibody fragments are subjected to a positive immunosorption against immunoglobulin G or fragments thereof which contain the Fd section. The use of Fc-free antigens e.g. Fab fragments is recommended in the positive immunosorption if a whole immunoglobulin has been used as the immunogen.

The immunosorption steps preferably additionally comprise (ii) at least one negative immunosorption against antigens or components thereof which are selected from immunoglobulin classes which are different from the first immunoglobulin class and the isolation of non-binding components of the composition. This negative immunosorption substantially reduces the cross-reactivity of the composition with the Fd section of the light chain and with the Fd section of the heavy chain of other immunoglobulin classes. In order to produce a composition that is specific for the Fd section of immunoglobulin G the negative immunosorption can be carried out against IgM, IgD, IgE or/and IgA or components thereof.

Optionally the immunosorption steps can furthermore comprise (iii) at least one negative immunosorption against antigens which are selected from the first immunoglobulin class of a species which is different from the species of the immunoglobulins in the positive immunosorption step (i) or components thereof and the isolation of non-binding components of the composition. It is preferable to carry out this step when the composition is to be used later in an immunoassay in which a detection antibody is used of the same immunoglobulin class but from another species. Preferably the positive immunosorption (i) is carried out with human immunoglobulins and the negative immunosorption (iii) is carried out with immunoglobulins of a non-human species e.g. the mouse. When a composition is produced that is specific for the Fd section of human immunoglobulin G the negative immunosorption step (iii) is carried out against immunoglobulin G of a non-human species.

The immunosorption steps are preferably carried out by adsorption chromatography on columns which contain the antigens used in each case in an immobilized form. Procedures for obtaining purified antigen preparations and for immobilizing antibodies or antibody fragments on a carrier material are well-known to a person skilled in the art (cf for example EP-A-0 394 819 in particular example 7).

The antibody or/and antibody fragment composition can be preferably used in an immunoassay for the selective class-specific determination of antibodies of the classes IgM, IgA, IgD or/and IgE in order to suppress the interferences caused by rheumatoid factors. For this a human serum or plasma sample which is to be measured in which it is intended to carry out a class-specific quantification of an antibody of a particular immunoglobulin class (e.g. IgM) which is directed towards a particular e.g. viral or bacterial antigen is for example admixed with an IgG-specific composition according to the invention preferably after a predilution step so that an elimination of interference by rheumatoid factors present in the sample is achieved. In the subsequent immunological detection only the specific IgM antibodies but not unspecific anti-IgG rheumatoid factors are detected in the sample. This enables a differential quantification of the specific content of a particular antibody class without interference by the presence of rheumatoid factors. The use of the composition according to the invention allows a one-step test procedure without a wash process.

Thus a subject matter of the present invention is also a method for the immunochemical determination of an analyte e.g. of specific antibodies from one or several selected immunoglobulin classes in a sample liquid which also contains rheumatoid factors which is characterized in that the determination is carried out in the presence of an anti-Fd composition as defined above. The composition is preferably added in an amount which corresponds to an at least 5-fold molar excess of the active components compared to the rheumatoid factors present in the sample liquid. The composition is preferably added in a 10- to 1000-fold molar excess. Optionally a pre-incubation is carried out for a period of preferably 5 to 60 min and particularly preferably of 10 to 30 min.

It is particularly preferable to carry out a determination of specific antibodies according to the principle of a heterogeneous immunoassay in the presence of a reactive solid phase and two receptors $R_1$ and $R_2$ capable of binding to the antibodies to be detected in which $R_1$ is bound to the solid phase or is capable of binding to the solid phase and $R_2$ is directly or indirectly labelled. The antibodies to be detected can then be determined, optionally after separating the solid phase and incubation liquid, by measuring the label in the solid phase or/and in the incubation liquid.

A conjugate of an antigen reacting specifically with the antibodies to be detected and a solid phase binding group can be used as the solid phase receptor $R_1$. In this case the receptor $R_2$ can either be an antigen reacting specifically with the antibodies to be detected or an antibody which recognizes the selected antibody class e.g. an anti-IgM antibody or an appropriate antibody fragment. The receptor $R_2$ can be directly or indirectly labelled i.e. it can be coupled to a labelling group or it can bind to a further receptor which in turn carries a labelling group.

It is also possible to use a conjugate of an antibody or an appropriate antibody fragment which recognizes the selected antibody class and a solid phase binding group as the solid phase receptor $R_1$. In this case an antigen which reacts specifically with the antibodies to be detected is used as the labelled receptor $R_2$.

One preferably uses a solid phase coated with streptavidin or avidin and a biotinylated receptor $R_1$ which can bind to this solid phase. Chromophore substances, radioactive isotopes, enzymes, NMR-labels or all other labels known from the state of the art can be used as the label. Luminescent metal complexes are preferably used in which the label can be measured by electrochemiluminescence. Examples of luminescent metal complexes and of methods and devices for the measurement of electrochemiluminescence are described in EP-A-0 199 804, EP-A-0 580 979, WO87/06706, WO90/05301, WO90/11511 and WO92/14138 to the disclosure of which reference is hereby made. Enzymes (e.g. peroxidase, alkaline phosphatase or β-galactosidase) are a further preferred label in which the label can be measured by detection of the respective enzymatic reaction.

The invention is further elucidated by the following examples and figures.

Figure 2:
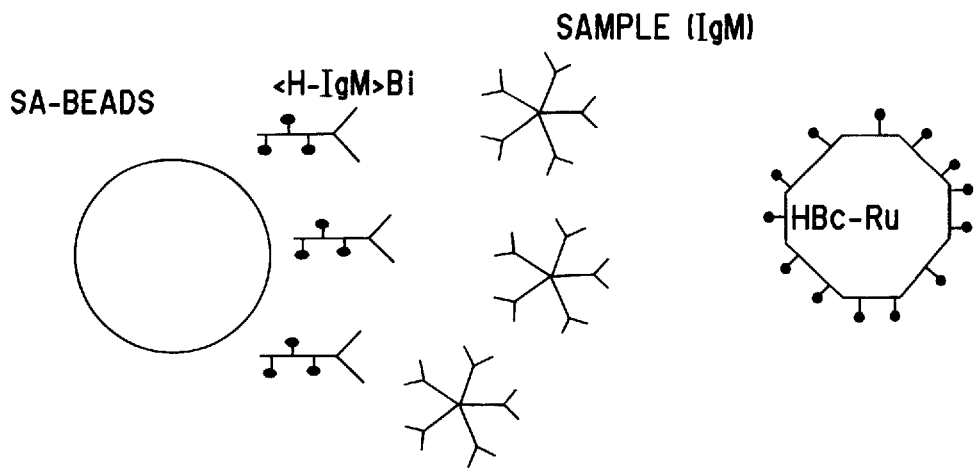
Figure 3:
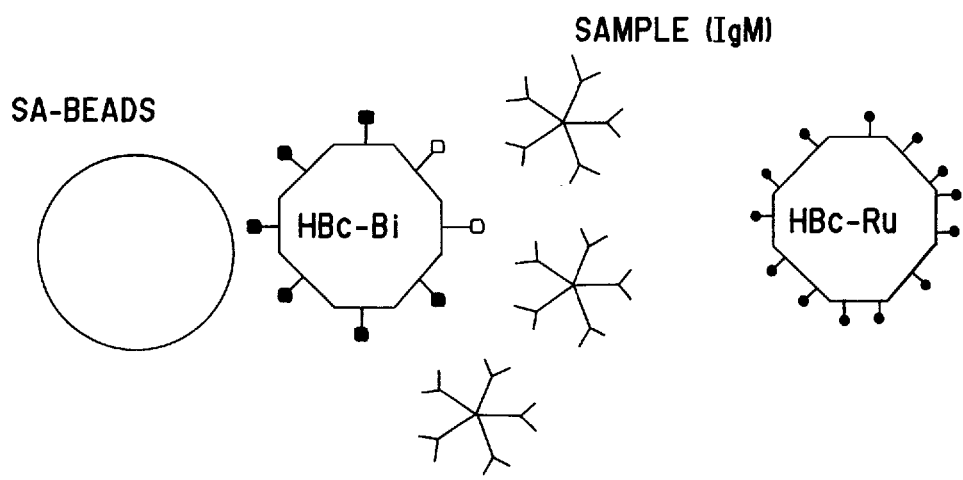

FIG. 1 shows the binding to human IgG (h-IgG) of an Fab fragment directed towards the Fd section of the heavy chain (<h–Fdγ>Fab), FIG. 2 shows the test principle of the class-specific detection of anti-HBc IgM by electrochemiluminescence carried out in example 3 and FIG. 3 shows a further test principle for a class-specific detection of anti-HBc IgM by electrochemiluminescence.

EXAMPLE 1

Production of a reagent according to the invention 1.1 Production of the Immunogen The immunoglobulin G fraction is purified from human serum by conventional standard methods. This purification can for example be carried out by aerosil delipidation, precipitation with ammonium sulfate, chromatography on DEAE-Sepharose FF and optionally immunosorption on immobilized IgG-specific polyclonal antibodies.

The immunoglobulin fraction purified in this manner is cleaved with papain into Fab and Fc fragments. The cleavage is preferably carried out at pH 7 and at 37° C. with an IgG concentration of 10 mg/ml, 40 mU/ml papain, 7 and 10 mmol/l cysteine. The Fab parts are purified of the Fc parts by DEAE-Sepharose FF chromatography and gel chromatography (e.g. Sephacryl TSK S200 and S300). The Fab fragments are preferably coupled to a carrier protein e.g. maleimide-activated Keyhole Limpet Haemocyanine (Boehringer Mannheim, Biochemica Catalogue, Order No. 1376438) in order to increase the immune reaction. For this Fab fragments are firstly activated with N-succinimidyl-S-acetylthiopropionate (SATP) in a molar ratio of 1:6. The carrier protein is coupled with the activated Fab fragment in a molar ratio of 1:1.

Fab fragments of other immunoglobulin classes (e.g. Fabμ) can be produced in a corresponding manner.

1.2 Immunization of Sheep

Sheep are immunized by standard methods using the immunogen produced in example 1. In an immune reaction these form polyclonal antibodies against human Fab which are directed towards the light chain part as well as towards the heavy chain part of human Fab.

Crude serum is withdrawn from the immunized sheep and the IgG fraction is isolated from this by the methods that have already been described.

1.3 Production of an Fd-Specific Reagent

The sheep immunoglobulin G fraction is proteolytically cleaved with papain. The Fab fragments are separated from the other cleavage products by means of DEAE anion exchange chromatography.

The components that are directed towards the Fd section of the heavy chain are purified from the total sheep Fab fraction by several immunosorption steps.

The components that are directed specifically towards the light chain (κ or λ) of human IgG can be removed by an optional several-fold passage through an immuno-adsorber on which IgM is immobilized because the constant region of the light chain of IgG and IgM is homologous. Whereas the components that are directed towards the light chain are adsorbed to the column, the components directed towards the Fd section of the heavy chain are located in the column eluant. A Spherosil column coupled with polyclonal IgM is used as the column. The application buffer is for example PBS/azide (50 mmol/l K-phosphate pH 7.5; 150 mmol/l NaCl; 0.1% sodium azide).

The non-binding fractions from the IgM column are pooled and subjected to a passage through a further immuno-adsorber which can optionally be repeated several times on which human IgG is immobilized. The specific fractions of anti-Fd sheep Fab can be separated on this column from unspecific sheep Fab fractions. The Fd-specific sheep Fab binds to this column and can be eluted with an elution buffer e.g. 1 mol/l propionic acid. The other components do not bind and are removed by washing the column with a suitable buffer (e.g. PBS/azide).

Furthermore interfering cross-reactivities with the mouse antibodies that are usually used in immunological tests as binding partners can be removed by an additional passage through an immuno-adsorber containing immobilized mouse IgG. The desired components of the preparation are in the column eluant.

The binding of an Fab fragment specific for human Fdγ (<h–Fdγ>Fab) to human IgG (h-IgG) is shown schematically in FIG. 1. The antigen binding sites of the h-IgG are in each case marked with arrows.

EXAMPLE 2

Examination of the Purity of the Reagent

Microtitre plates (MTP) from the Nunc Co. were coated with sheep Fab-specific rabbit IgG as a solid phase or capture antibody (10 μg/ml rabbit IgG, sodium carbonate buffer pH 9.6, re-coating with 1% bovine serum albumin in PBS buffer). The reagent to be analysed is preincubated as a sample with increasing concentrations (e.g. 0 to 10 μg/ml) in each case of a preparation of purified human Fabγ fragments or human Fabμ fragments and subsequently transferred to the coated MTP (sample volume 200 μl, incubated for 2 h at room temperature, buffer PBS containing 1% bovine serum albumin).

The sheep Fab components of the sample that are specific for human Fdγ are also bound to the solid phase as are impurities that may be present which are directed towards the light immunoglobulin chain and which may not have been completely separated during the purification. Non-bound components are removed by washing three times with PBS buffer.

A horseradish peroxidase coupled to human Fabγ (200 μl, 50 mU/ml) is used as the detection reagent. After washing three times with PBS buffer the enzymatic activity of the bound peroxidase conjugate is developed by incubating for, 1 h at room temperature with the substrate ABTS® and subsequently measured photometrically at 405 nm. Of the sheep Fab components of the sample that were previously bound to the solid phase only those components which are directed towards human Fab are detected by the enzyme marker conjugate. As a result a positive signal of 1000 to 3000 mA is produced in the control without addition of Fabμ and Fabγ. This corresponds to the total amount of the sheep Fab directed towards human Fab which is present in a preparation to be examined. In the samples to which increasing amounts of human Fabγ had been added, the masking of the Fdγ-specific sheep Fab results in an increasing displacement of the conjugate and thus to a measured signal curve which tends towards 0 or towards a blank value. In contrast in the samples to which increasing amounts of human Fabμ had been admixed only the sheep Fab components that are directed towards the light chain are masked so that in this case a decrease in the signal only occurs when such undesired components are still present in the sheep Fab preparation. The difference between the two displacement curves would in the latter case correspond to the actual amount of Fdγ-specific sheep Fab in the preparation.

The measurement of the sample without added human Fabμ or Fabγ results in an absorbance of 1600 mA. The sample +Fabμ results in an absorbance of 1500 mA. The sample +Fabγ results in an absorbance of 150 mA.

It can be seen that four samples (1, 3, 4 and 5) apparently show a positive reaction without addition of interference-eliminating reagent or only when aggregated IgG is added. In the presence of the anti-Fd reagent only sample No. 1 shows a positive reaction. The positive signal in samples 3–5 in the absence of the anti-Fd reagent is therefore a false-positive signal and only due to the presence of high concentrations of rheumatoid factors (RF).

As can be seen from the table the addition of anti-Fd reagent (<Fdγ>) leads to a complete elimination of interference of the rheumatoid sera in contrast to the addition of aggregated IgG according to the state of the art. This result shows that the anti-Fd reagent has a significantly improved interference elimination compared to unspecific IgG known from the state of the art.

TABLE 1

| | without <Fdγ> aggregated IgG in the sample | | with <Fdγ> aggregated IgG in the sample | | |
|---|---|---|---|---|---|
| Sample No. | − <HBc> IgM [U/ml] | + <HBc> IgM [U/ml] | − <HBc> IgM [U/ml] | + <HBc> IgM [U/ml] | RF [IU/ml] |
| 1 | 112 | 102 | 128 | 134 | 1.30 |
| 2 | 0 | 0 | 1 | 1 | 1.04 |
| 3 | 1856 | 602 | 0.3 | 0.5 | 158.97 |
| 4 | 157 | 52 | 0 | 0 | 126.35 |
| 5 | 182 | 24 | 0 | 0 | 146.14 |

EXAMPLE 3

Detection of Anti-HBc-IgM by Electrochemiluminescence in the Presence of Rheumatoid Factors An apparatus was used for the measurement as described in WO90/05302. The test principle is shown in FIG. 2 and is based on the use of a biotinylated antibody that is specific for human IgM (<H–IgM>Bi) and a HBc antigen which is directly labelled with a ruthenium complex (HBc-Ru). Alternatively it is also possible to use an indirectly labelled HBc antigen (by binding a ruthenylated anti-HBc antibody). The ruthenium complex and the techniques used for coupling to the HBc antigen or to the antibody are described in EP-A-0 199 804.

A further test principle is shown in FIG. 3. It is based on the use of a biotinylated HBc antigen (HBc-Bi) and a ruthenium-labelled HBc antigen (HBc-Ru).

The procedure was as follows:

90 μl of a solution of unspecific human IgM (11 μg/ml) with or without aggregated IgG (0.5 mg/ml) or anti-Fdγ reagent (2 mg/ml) was admixed with 10 μl of 1:100 prediluted samples or standards and incubated for 10 min at 37° C.

Subsequently 100 μl of a solution which contained ruthenium-labelled HBc antigen (0.5 μg/ml) and a biotinylated anti-human IgM antibody (2 μg/ml) and 40 μl streptavidin-coated magnetic particles (Dynal Co., 720 μg/ml) was added, the mixture was subsequently incubated for a further 10 min. at 37° C., then transferred with assay buffer (200 mmol/l phosphate, pH 6.8, 0.1% polydocanol, 0.1% Oxaban A, 160 mmol/l tripropylamine) into the measuring cell thermostated at 28° C. and measured there.

The anti-HBc IgM concentration in the samples was subsequently determined based on a calibration curve. The results in terms of concentration are shown in Table 1.

We claim:

1. A method for reducing interference in an immunochemical determination of an analyte in a sample liquid wherein said sample liquid contains rheumatoid factors, comprising
    adding an interference reducing reagent to said sample, wherein said interference reducing reagent consists essentially of at least two different antibodies and/or antibody fragments which are specific for the Fd fragment of the heavy chain of immunoglobulins from at least one of the classes selected from the group consisting of IgG, IgM, IgA, IgD and IgE, wherein said antibodies partially or completely mask the ability of said immunoglobulins to bind antigens, and
    carrying out said immunochemical determination.

2. The method according to claim 1, wherein said analyte is at least one antibody selected from the group consisting of antibodies of the classes IgM, IgA, IgD and IgE.

3. The method according to claim 2, wherein said analyte is an IgM class antibody.

4. The method according to claim 1, wherein the reagent is added in an amount which corresponds to an at least 5-fold molar excess of the antibodies and/or antibody fragments relative to rheumatoid factors present in the sample liquid.

5. The method according to claim 4, wherein the composition is added in a 10-fold to 1000-fold molar excess.

6. The method according to claim 1, further comprising pre-incubating the sample liquid with the reagent for a period of 5 to 60 min prior to carrying out the immunochemical determination.

7. The method according to claim 1, wherein the immunochemical determination is carried out according to the principle of a heterogeneous immunoassay in the presence of a reactive solid phase and two receptors $R_1$ and $R_2$ capable of binding to the analyte to be detected, wherein $R_1$ is bound to the solid phase or is capable of binding to the solid phase and $R_2$ is directly or indirectly labelled and the analyte to be detected is determined by measuring any label in the solid phase and/or in the incubation liquid.

8. The method according to claim 7, wherein said analyte is an antibody, and wherein a conjugate of an antigen which specifically reacts with the antibody to be detected and a solid phase binding group is used as receptor $R_1$ and an antigen which specifically reacts with the antibody to be detected is used as receptor $R_2$ which is directly or indirectly labelled.

9. The method according to claim 7, wherein said analyte is an antibody, wherein a conjugate of an antigen which specifically reacts with the antibody to be detected and a solid phase binding group is used as receptor $R_1$ and an antibody which recognizes a selected antibody class and is directly or indirectly labelled or an antibody fragment is used as receptor $R_2$.

10. The method according to claim 7, wherein said analyte is an antibody, and wherein a conjugate of an antibody or an antibody fragment which recognizes a selected antibody class and a solid phase binding group is used as receptor $R_1$ and an antigen which is directly or indirectly labelled and specifically reacts with the antibody to be detected is used as receptor $R_2$.

11. The method according to claim 7, wherein a reactive solid phase coated with streptavidin or avidin and a biotinylated receptor $R_1$ are used.

12. The method according to claim 7, wherein a luminescent metal complex is used as the label and the label is measured by electrochemiluminescence.

13. The method according to claim 7, wherein an enzyme is used as the label and the label is measured by detection of an enzymatic reaction.

14. The method according to claim 1, wherein said immunochemical determination is carried out in one step.

15. A method for reducing interference in an immunoassay for the selective class determination of a class of antibodies selected from the group consisting of IgM, IgA, IgD, and/or IgE in a sample liquid, wherein said sample liquid contains rheumatoid factors, comprising the steps of:

adding an interference reducing reagent to said sample, wherein said interference reducing reagent consists essentially of at least two different antibodies and/or antibody fragments which are specific for the Fd fragment of the heavy chain of immunoglobulins from at least one of the classes selected from the group consisting of IgG, IgM, IgA, IgD and IgE, wherein said interference reducing reagent partially or completely masks the ability of said immunoglobulins to bind antigens, and wherein said interference reducing reagent is not specific for the class of antibodies to be determined, and carrying out said immunoassay.

* * * * *